United States Patent
Irving et al.

(10) Patent No.: US 11,948,680 B2
(45) Date of Patent: Apr. 2, 2024

(54) SYSTEMS AND METHODS TO DISTRIBUTE CARDIAC DEVICE ADVISORY DATA

(71) Applicant: Murj, Inc., Santa Cruz, CA (US)

(72) Inventors: Christopher S. Irving, Santa Cruz, CA (US); Eddy Luten, Canton, MS (US); Richard Todd Butka, Santa Cruz, CA (US)

(73) Assignee: MURJ, INC., Santa Cruz, CA (US)

( * ) Notice: Subject to any disclaimer, the term of this patent is extended or adjusted under 35 U.S.C. 154(b) by 0 days.

(21) Appl. No.: 17/953,144

(22) Filed: Sep. 26, 2022

(65) Prior Publication Data

US 2023/0298744 A1   Sep. 21, 2023

Related U.S. Application Data

(63) Continuation of application No. 17/654,949, filed on Mar. 15, 2022, now Pat. No. 11,456,072.

(51) Int. Cl.
*G08B 1/08* (2006.01)
*G16H 10/60* (2018.01)
(Continued)

(52) U.S. Cl.
CPC .............. *G16H 40/60* (2018.01); *G16H 10/60* (2018.01); *G16H 20/40* (2018.01); *G16H 80/00* (2018.01)

(58) Field of Classification Search
CPC ........ G16H 40/60; G16H 10/60; G16H 20/40; G16H 80/00
(Continued)

(56) References Cited

U.S. PATENT DOCUMENTS

| 4,783,803 A | 11/1988 | Baker et al. |
| 5,798,752 A | 8/1998 | Buxton et al. |

(Continued)

FOREIGN PATENT DOCUMENTS

| JP | 2001101306 A | 4/2001 |
| JP | 2005063253 A | 3/2005 |

(Continued)

OTHER PUBLICATIONS

Dec. 27, 2022—U.S. Non-Final Office Action—U.S. Appl. No. 17/809,509, 24 pages.

(Continued)

*Primary Examiner* — Tai T Nguyen
(74) *Attorney, Agent, or Firm* — Polsinelli PC

(57) ABSTRACT

Systems and methods include a cardiac device advisory management platform to receive and distribute data related to advisory notification(s) for an implanted cardiac device. Advisory notification data includes a device identifier and/or a lead identifier corresponding to the advisory notification. Upon receiving the advisory notification data, the clinic matches the device identifier and/or the lead identifier with patient data for patients enrolled with the clinic. One or more action indicators for various workflow procedures are generated and presented at a clinic user interface (UI) of the clinic device. Clinician inputs are received via the clinic UI to perform steps in response to the advisory notification, such as reviewing patient information, scheduling an in-office visit, and/or sending a notification to a patient device. A clinic behavior analysis is performed on the clinician inputs to generate information regarding the impact of the advisory notifications on the clinic workflow procedures.

16 Claims, 12 Drawing Sheets

(51) Int. Cl.
*G16H 20/40* (2018.01)
*G16H 40/60* (2018.01)
*G16H 80/00* (2018.01)

(58) Field of Classification Search
USPC .................................................. 340/539.125
See application file for complete search history.

(56) References Cited

U.S. PATENT DOCUMENTS

| | | | |
|---|---|---|---|
| D571,818 S | 6/2008 | Loehr et al. | |
| D579,020 S | 10/2008 | Aliaga | |
| D606,088 S | 12/2009 | Yokouchi et al. | |
| D617,808 S | 6/2010 | Thompson et al. | |
| 7,761,507 B2 | 7/2010 | Herf et al. | |
| 7,805,199 B2 * | 9/2010 | KenKnight | A61N 1/36514 607/32 |
| 8,060,821 B2 | 11/2011 | Seymour et al. | |
| 8,112,151 B1 | 2/2012 | Cogan et al. | |
| D703,688 S | 4/2014 | Choi | |
| D731,520 S | 6/2015 | Xiong et al. | |
| D732,051 S | 6/2015 | Jeong et al. | |
| D741,882 S | 10/2015 | Shmilov et al. | |
| D749,623 S | 2/2016 | Gray et al. | |
| D753,670 S | 4/2016 | Tian | |
| D757,065 S | 5/2016 | Jeon et al. | |
| D761,842 S | 7/2016 | Johnson et al. | |
| D763,879 S | 8/2016 | Worrell et al. | |
| D764,501 S | 8/2016 | Dias et al. | |
| D768,707 S | 10/2016 | Gagnier | |
| D771,649 S | 11/2016 | Eze et al. | |
| D777,177 S | 1/2017 | Chen et al. | |
| D777,195 S | 1/2017 | Dain et al. | |
| D779,514 S | 2/2017 | Baris et al. | |
| D780,797 S | 3/2017 | Kisielius et al. | |
| D781,889 S | 3/2017 | Wills et al. | |
| D781,905 S | 3/2017 | Nakaguchi et al. | |
| D782,526 S | 3/2017 | Rind et al. | |
| D783,030 S | 4/2017 | Lee et al. | |
| D785,022 S | 4/2017 | Vazquez et al. | |
| D788,128 S | 5/2017 | Wada | |
| D789,377 S | 6/2017 | Vazquez | |
| D789,397 S | 6/2017 | Lee et al. | |
| D789,982 S | 6/2017 | Christiana et al. | |
| D792,424 S | 7/2017 | Meegan et al. | |
| D792,426 S | 7/2017 | Theodore et al. | |
| D794,047 S | 8/2017 | Gandhi et al. | |
| D796,523 S | 9/2017 | Bhandari et al. | |
| D798,320 S | 9/2017 | Gouvernel et al. | |
| D800,741 S | 10/2017 | Rhodes | |
| D803,845 S | 11/2017 | Arora | |
| D805,525 S | 12/2017 | Dascola et al. | |
| D806,097 S | 12/2017 | Rahn et al. | |
| D807,379 S | 1/2018 | Pahwa et al. | |
| D807,385 S | 1/2018 | Olsen et al. | |
| D807,900 S | 1/2018 | Raji et al. | |
| D807,911 S | 1/2018 | Zhou et al. | |
| D808,399 S | 1/2018 | Derby et al. | |
| D808,400 S | 1/2018 | Coren | |
| D808,981 S | 1/2018 | Hazam et al. | |
| D822,678 S | 7/2018 | Wu et al. | |
| D823,326 S | 7/2018 | Pinzon Garcia et al. | |
| D823,327 S | 7/2018 | Durkan et al. | |
| D823,860 S | 7/2018 | Wiffen et al. | |
| D829,229 S | 9/2018 | Durkan et al. | |
| D830,382 S | 10/2018 | Marohn | |
| D832,296 S | 10/2018 | Golden et al. | |
| D833,459 S | 11/2018 | Blechschmidt et al. | |
| D835,138 S | 12/2018 | Edgington, Jr. | |
| D840,426 S | 2/2019 | Dieken et al. | |
| D841,017 S | 2/2019 | Bathla | |
| D841,675 S | 2/2019 | Hoffman et al. | |
| D843,403 S | 3/2019 | Casse et al. | |
| D845,973 S | 4/2019 | Jaycobs | |
| D845,974 S | 4/2019 | Cooperman et al. | |
| D847,165 S | 4/2019 | Kolbenheyer | |
| D849,014 S | 5/2019 | Senders | |
| D849,029 S | 5/2019 | Cooperman et al. | |
| D849,773 S | 5/2019 | Jiang et al. | |
| 10,289,660 B2 | 5/2019 | Karunamuni et al. | |
| D853,412 S | 7/2019 | Hofner et al. | |
| D853,420 S | 7/2019 | Ambrose et al. | |
| D854,030 S | 7/2019 | Dascola et al. | |
| D854,565 S | 7/2019 | McLaughlin et al. | |
| D860,237 S | 9/2019 | Li et al. | |
| D860,239 S | 9/2019 | Lirov et al. | |
| D867,389 S | 11/2019 | Jamison et al. | |
| D869,488 S | 12/2019 | Storr | |
| D870,762 S | 12/2019 | Mendoza Corominas et al. | |
| D872,117 S | 1/2020 | Kobayashi et al. | |
| D874,486 S | 2/2020 | Ragland et al. | |
| D875,747 S | 2/2020 | Iida et al. | |
| D875,761 S | 2/2020 | Heffernan et al. | |
| D876,454 S | 2/2020 | Knowles et al. | |
| D877,167 S | 3/2020 | Knowles et al. | |
| D879,112 S | 3/2020 | Hejazi et al. | |
| D879,134 S | 3/2020 | Jones | |
| D880,513 S | 4/2020 | Wang et al. | |
| D881,908 S | 4/2020 | Sunil et al. | |
| D881,910 S | 4/2020 | Lin | |
| D888,739 S | 6/2020 | Christiana et al. | |
| D898,056 S | 10/2020 | Olson | |
| D905,734 S | 12/2020 | Christiana et al. | |
| D906,358 S | 12/2020 | Christiana et al. | |
| D924,258 S | 7/2021 | Klimer et al. | |
| 2001/0039504 A1 | 11/2001 | Linberg et al. | |
| 2001/0051765 A1 | 12/2001 | Walker et al. | |
| 2002/0056575 A1 | 5/2002 | Keely et al. | |
| 2002/0082665 A1 | 6/2002 | Haller et al. | |
| 2002/0089547 A1 | 7/2002 | Huapaya | |
| 2004/0008224 A1 | 1/2004 | Molander et al. | |
| 2004/0071344 A1 | 4/2004 | Lui et al. | |
| 2005/0021370 A1 | 1/2005 | Riff et al. | |
| 2005/0065445 A1 | 3/2005 | Arzbaecher et al. | |
| 2005/0278140 A1 | 12/2005 | Wang | |
| 2007/0016857 A1 | 1/2007 | Polleck et al. | |
| 2007/0060797 A1 | 3/2007 | Ball et al. | |
| 2007/0135855 A1 | 6/2007 | Foshee et al. | |
| 2008/0007570 A1 | 1/2008 | Wessel et al. | |
| 2008/0109051 A1 | 5/2008 | Splinter et al. | |
| 2009/0187426 A1 | 7/2009 | Kerstna et al. | |
| 2010/0005411 A1 | 1/2010 | Duncker et al. | |
| 2010/0134353 A1 | 6/2010 | Van Diggelen | |
| 2011/0004277 A1 | 1/2011 | Johnson et al. | |
| 2011/0054264 A1 * | 3/2011 | Fischell | G16H 40/67 600/300 |
| 2011/0119212 A1 | 5/2011 | De Bruin et al. | |
| 2012/0095300 A1 | 4/2012 | McNair | |
| 2012/0143017 A1 | 6/2012 | Snyder | |
| 2012/0194558 A1 | 8/2012 | Dykes et al. | |
| 2012/0223889 A1 | 9/2012 | Medlock et al. | |
| 2012/0288881 A1 | 11/2012 | Liu | |
| 2012/0290599 A1 | 11/2012 | Tian et al. | |
| 2013/0035209 A1 | 2/2013 | Gilley et al. | |
| 2013/0232437 A1 | 9/2013 | Kim | |
| 2013/0274705 A1 * | 10/2013 | Burnes | A61M 5/1723 604/503 |
| 2013/0317852 A1 | 11/2013 | Worrell et al. | |
| 2015/0227691 A1 | 8/2015 | Bhattacharya et al. | |
| 2015/0295914 A1 | 10/2015 | Kelishadi | |
| 2015/0324549 A1 | 11/2015 | Nearhood et al. | |
| 2015/0370920 A1 | 12/2015 | Van Os et al. | |
| 2016/0246931 A1 | 8/2016 | Rajan et al. | |
| 2016/0292456 A1 | 10/2016 | Dubey et al. | |
| 2016/0306929 A1 | 10/2016 | Butka et al. | |
| 2017/0262605 A1 | 9/2017 | Wadhwa et al. | |
| 2017/0312534 A1 | 11/2017 | Cao et al. | |
| 2019/0026838 A1 | 1/2019 | Tan et al. | |
| 2019/0083030 A1 | 3/2019 | Thakur et al. | |
| 2019/0109757 A1 | 4/2019 | Oliveira et al. | |
| 2019/0213544 A1 | 7/2019 | Spirig et al. | |

(56) References Cited

U.S. PATENT DOCUMENTS

2022/0144427 A1\* 5/2022 Vernon ............... G08G 5/0034
2022/0280047 A1\* 9/2022 Stadler ............... A61B 5/6898

FOREIGN PATENT DOCUMENTS

JP          2005319151 A      11/2005
WO     WO-2010051175 A1      5/2010

OTHER PUBLICATIONS

ANGI71., "Vector Buttons Blue and White," May 17, 2008, Retrieved from the Internet: URL: https://www.istockphoto.com/vector/vector-buttons-blue-and-white-gray-gm95492721-6143274, 5 pages.
E. T. van der Velde, H. Foeken, T. Witteman, L. van Erven and M. J. Schalij, "Integration of remote monitoring data into the hospital electronic health record system: Implementation based on international standards," 2011 Computing in Cardiology, 2011, pp. 581-584 (Year: 2011).
International Search Report and Written Opinion, PCT/US2016/028470, dated Jul. 22, 2016, 10 pages.
International Search Report and Written Opinion—PCT/US2022/073231, dated Sep. 27, 2022, 9 pgs.
JP Office Action, JP2020-548891_ dated Aug. 31, 2021.
Notice of Allowance for U.S Appl. No. 15/134,130, dated Feb. 21, 2019, 8 pages.
Notice of Allowance for U.S. Appl. No. 17/654,949, dated May 9, 2022, 8 pages.
Notice of Allowance for U.S. Appl. No. 17/654,949, dated May 23, 2022, 2 pages.
Notice of Allowance for U.S. Appl. No. 29/643,240, dated Aug. 10, 2020, 7 pages.
Notice of Allowance for U.S. Appl. No. 29/643,241, dated Aug. 12, 2020, 8 pages.
Notice of Allowance for U.S. Appl. No. 29/643,242, dated May 22, 2020, 7 pages.
Notice of Allowance for U.S. Appl. No. 29/643,244, dated Aug. 10, 2020, 7 pages.
Notice of Allowance for U.S. Appl. No. 29/763,698, dated Jun. 8, 2022, 6 pages.
Notice of Allowance for U.S. Appl. No. 29/764,234, dated Jul. 8, 2022, 7 pages.
Office Action for U.S Appl. No. 15/134,130, dated May 9, 2018, 18 pages.
Office Action for U.S. Appl. No. 16/889,210, dated Nov. 18, 2022, 18 pages.
Office Action for U.S. Appl. No. 17/809,509, dated Apr. 17, 2023, 19 pages.
Office Action for U.S. Appl. No. 29/763,144, dated Oct. 21, 2022, 6 pages.
Office Action for U.S. Appl. No. 29/763,698, dated Sep. 7, 2021, 6 pages.
Office Action for U.S. Appl. No. 29/764,234, dated Sep. 7, 2021, 7 pages.
Shlain A., "Common Icon Set," Apr. 26, 2015, Retrieved from the Internet: URL: https://www.iconfinder.com/iconsets/common-3, 1 Page.
StackExchange "Dynamic Progress Indicator," Mar. 25, 2014, Retrieved from the Internet: URL: https://ux.stackexchange.com/questions/54570/dynamic-progress-indicator, 2 pages.
Staudacher I., et al., "Fully Digital Data Processing During Cardiovascular Implantable Electronic Device Follow-Up in a High-Volume Tertiary Center," European Journal of Medical Research, Oct. 11, 2017, vol. 22, No. 1, 9 pages, DOI:10.1186/s40001-017-0284-7.
U.S. Appl. No. 29/643,240, filed Apr. 5, 2018, Butka et al.
U.S. Appl. No. 29/643,241, filed Apr. 5, 2018, Butka et al.
U.S. Appl. No. 29/643,242, filed Apr. 5, 2018, Butka et al.
U.S. Appl. No. 29/643,244, filed Apr. 5, 2018, Butka et al.

\* cited by examiner

SYSTEMS AND METHODS TO DISTRIBUTE CARDIAC DEVICE ADVISORY DATA

CROSS REFERENCE TO RELATED APPLICATIONS

The present application is a continuation application of U.S. application Ser. No. 17/654,949, filed Mar. 15, 2022, now U.S. Pat. No. 11,456,072, and titled "Systems and Methods to Distribute Cardiac Device Advisory Data," which is hereby incorporated by reference in its entirety herein.

FIELD

Aspects of the presently disclosed technology relate generally to patient device monitoring and, more particularly, to systems and methods to distribute advisory information for cardiac implantable electronic devices.

BACKGROUND

Implantable medical devices are regularly used to treat and/or monitor a variety of medical conditions. For example, cardiac implantable electronic devices (CIED), such as implantable cardioverter defibrillators (ICDs) are often utilized to regulate and monitor cardiac functions. CIEDs may include, without limitation: pacemakers (PMs), which prevent slow heart rates using low-energy electrical pulses; implantable cardioverter defibrillators (ICDs), which are used to detect abnormal heart arrhythmias and deliver lifesaving shocks to prevent sudden cardiac arrest; implantable loop recorders (ILRs) and implantable cardiac monitors (ICMs), which continuously monitor cardiac data and transmit data to the clinic as prescribed by a clinician and at the patient's discretion; and the like. Such CIEDs store and may periodically transmit information relating to the operation of the device outside the body for analysis, programming, and/or the like. More particularly, CIEDs store and transmit information for in-office or remote monitoring by a medical provider.

Advisories are regularly issued for these CIEDs and their components (e.g., leads, batteries, etc.). The advisories are issued from various manufacturers to a Federal Drug Administration (FDA) office which, in turn, releases the advisory to the public-usually six to eight weeks after the advisories are initially released from the manufacturer. The onus is on care providers to update their records based on the FDA releases and/or manufacturer releases. Care providers usually have complex patient records systems that make it difficult to easily manage the variety of different advisories and documentation they require. Furthermore, manufacturers are unaware of the downstream impacts (e.g., amount of work) their advisories cause and are ill-equipped to gather such information.

It is with these observations in mind, among others, that various aspects of the present disclosure were conceived and developed.

SUMMARY

Implementations described and claimed herein address the foregoing problems by providing systems and methods for remote cardiac patient monitoring. In some examples, a method to manage cardiac patient devices comprises: receiving cardiac patient data including one or more device identifiers associated with one or more implanted cardiac devices to enroll one or more patients using the one or more implanted cardiac devices with a clinic; determining advisory notification data associated with an advisory notification for at least one implanted cardiac device of the one or more implanted cardiac devices; causing the advisory notification data to be stored at an advisory notification database; causing a clinic device associated with the clinic to present one or more indication of the advisory notification based on the advisory notification data, the one or more indication including an action indicator corresponding to a status of a patient represented by a patient identifier; receiving a clinician input, at the clinic device, corresponding to the patient identifier; and causing a change in the status to be presented at the clinic device responsive to the clinician input.

In some instances, the action indicator corresponds to one or more of: an in-progress indicator; an acknowledged indicator; a monitoring indicator; or a resolved indicator. The clinician input can be a first clinician input; and the method can further comprise receiving a second clinician input, responsive to the action indicator, causing the status of the patient to be: associated with action-in-progress for the advisory notification, opted-out of tracking for the advisory notification; opted-in for tracking for the advisory notification; or monitored for other advisory notifications. The method can further comprise storing clinic action data in a clinic action database corresponding to a plurality of clinician inputs associated with the advisory notification including the first clinician input or the second clinician input; and outputting results of a clinic behavior analysis, particular to the advisory notification, corresponding to the clinic based on the clinic action data. Additionally, the method can comprise presenting, at the clinic device, a link extracted from the advisory notification directed to a website of a manufacturer associated with the at least one implanted cardiac device. The advisory notification can be a first advisory notification with a first format corresponding to a first device manufacturer; the one or more indication can be a first indication; and the method can further comprise: receiving a second advisory notification with a second format corresponding to a second device manufacturer that is different from the first device manufacturer; causing the second advisory notification to be stored at the advisory notification database; and causing the clinic device to present a second indication of the second advisory notification.

In some examples, the advisory notification is a first advisory notification for a particular cardiac device model; the one or more indication is a first indication; and the method further comprises: receiving a second advisory notification for the particular cardiac device model; and causing the clinic device to present, at a clinic user interface (UI), a second indication of the second advisory notification simultaneously with the first indication of the first advisory notification. Furthermore, by way of example, the advisory notification is a first advisory notification for a first lead of the at least one implanted cardiac device; the one or more indication is a first indication; and the method further comprises: receiving second advisory notification data corresponding to a second lead of the at least one implanted cardiac device; and causing the clinic device to present, at a clinic user interface (UI), a second indication of the second advisory notification data simultaneously with the first indication of the first advisory notification. Moreover, the one or more indication of the advisory notification can include a list of patients associated with a device identifier included in the advisory notification. The method can further comprise determining an advisory class level of the advisory notification, the advisory class level being a first class level, a second class level, or a third class level, wherein the action indicator corresponds to the advisory class level.

In some instances, a method to manage cardiac patient devices comprises: receiving cardiac patient data including a plurality of device identifiers associated with a plurality of implanted cardiac devices to enroll a plurality of patients with a clinic; determining advisory notification data associated with an advisory notification for at least one implanted cardiac device of the plurality of implanted cardiac devices; causing a clinic device associated with the clinic to present a clinic user interface (UI) with one or more indication of the advisory notification based on the advisory notification data, the one or more indication including an action indicator corresponding to a status of a patient represented by a patient identifier; receiving a clinician input, at the clinic UI in response to the one or more indication; and causing additional advisory information related to the advisory notification to be presented at the clinic device responsive to the clinician input.

In some examples, the method includes extracting an implanted cardiac device model identifier or a lead identifier from the advisory notification; and storing the implanted cardiac device model identifier or the lead identifier associated with the advisory notification at an advisory notification database accessible to the clinic device. Moreover, the method can further comprise receiving device interrogation data for the at least one implanted cardiac device during an in-office visit of the patient; and presenting the action indicator corresponding to the status of the patient at least partly in response to the device interrogation data. The method can further comprise transmitting, from the clinic device and to a cardiac device management platform, a patient notification corresponding to the advisory notification at least partly in response to the clinician input; and/or storing the advisory notification data at an advisory notification database to make the advisory notification data accessible to the clinic device within 48 hours of an advisory date included in the advisory notification. Furthermore, receiving the advisory notification can include receiving a manufacturer release of the advisory notification that includes: an advisory title; an advisory date; an advisory description; a manufacturer page link; an advisory classification; a recommended action; a device model or lead model; a device number; a device type; and a device serial number.

In some instances, a method to manage cardiac patient devices comprises: receiving cardiac patient data including a plurality of device identifiers associated with a plurality of implanted cardiac devices to enroll a plurality of patients with a clinic; determining advisory notification data associated with an advisory notification for at least one implanted cardiac device of the plurality of implanted cardiac devices; causing a clinic device associated with the clinic to present a clinic user interface (UI) with one or more indication of the advisory notification based on the advisory notification data, the one or more indication including an action indicator corresponding to a status of a patient represented by a patient identifier; receiving a clinician input at the clinic UI, in response to the one or more indication, selecting a patient of the plurality of patients; and causing additional information related to the patient to be presented at the clinic device responsive to the clinician input.

In some scenarios, the one or more indication includes a list of patients having the at least one implanted cardiac device corresponding to the advisory notification; and the method further comprises: receiving a patient filtering clinician input based on a patient characteristic; and causing, responsive to the patient filtering clinician input, a filtered list of the patients having the at least one implanted cardiac device corresponding to the advisory notification to be presented at the clinic device. The patient filtering clinician input can indicate a particular clinic site associated with the clinic. Additionally or alternatively, the patient filtering clinician input can indicate a patient illness characteristic shared by multiple patients of the plurality of patients.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Figure 1:
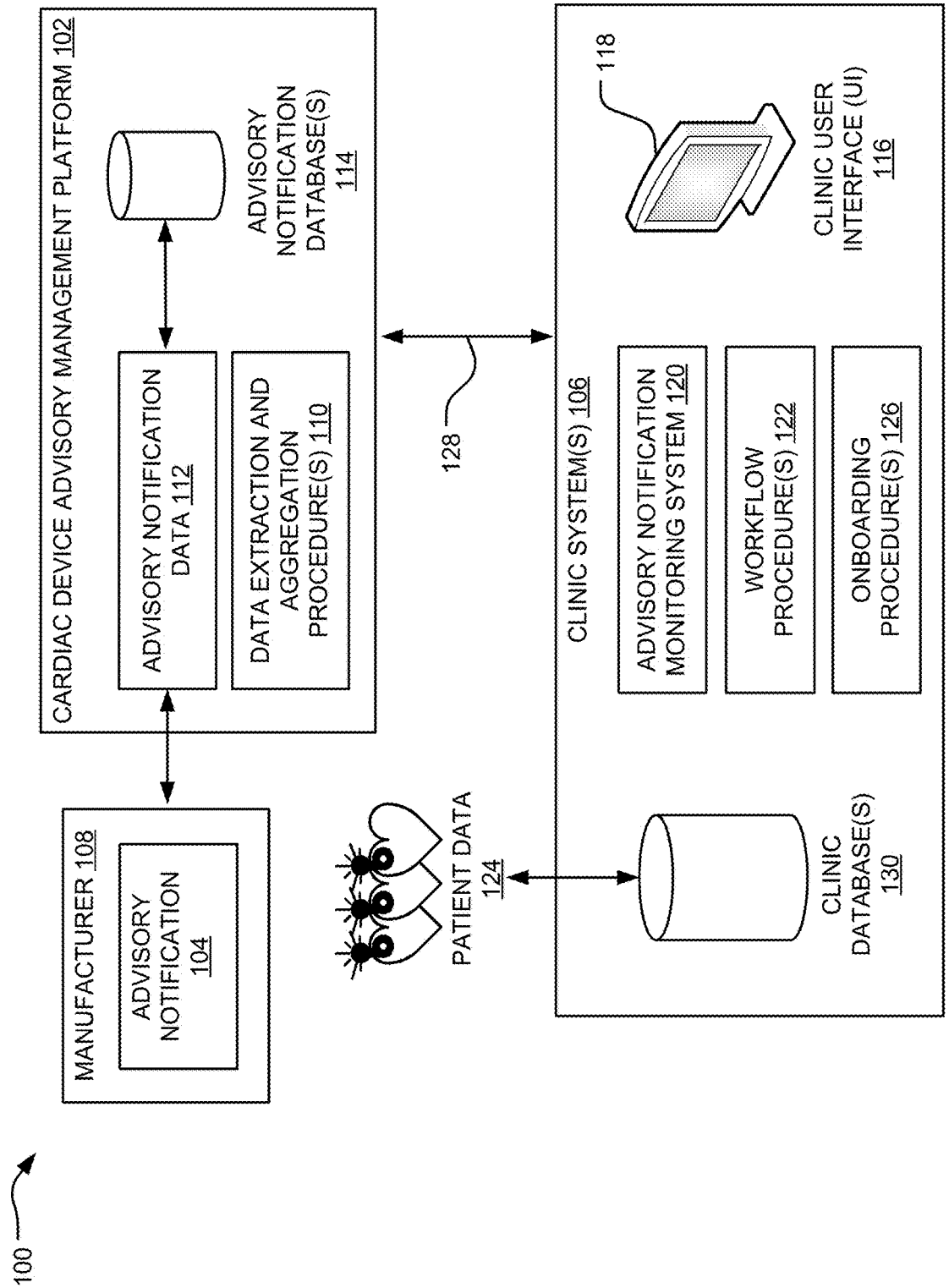
FIG. 1 illustrates an example system to track and distribute advisory notification data using a cardiac device advisory management platform.

Aspects of the present disclosure involve systems and methods for tracking and distributing data for advisory notifications released by device and/or lead manufacturers. The advisory notification can be a warning or a recall of the device and can specify a recommended action the clinicians to take. The systems disclosed herein assist clinics in properly identifying and managing and document actions to be taken for these advisories. As such, challenges related to identifying and tracking a dynamic patient population with different device types and serial numbers are overcome. For instance, the system can improve tracking for work that is completed and in progress and can assist clinic personnel in managing different stages of the workflow. The systems and methods improve timeliness by disseminating advisory notification recall information directly from the manufacturers to clinic systems, making it actionable within 48 hours of the advisory release date.

The system can include a cardiac device advisory management platform that receives the advisory notification from the manufacturer and extracts advisory notification data from the advisory notification. The advisory notification data can be stored and/or sent by the platform to a clinic device operating a clinic user interface (UI) to improve various workflow procedures at the clinic. For instance, the clinic systems can operate an advisory notification monitoring system provided by the cardiac advisory management platform which integrates the advisory notification data into workflows by generating different action indicators to correspond to different types of advisory actions. Additionally, interfaces generated at the clinic device can improve the clinic workflows, such as an advisory status interface, a data extraction interface, an advisory administration interface, a patient panel, and a patient docket advisory notice interface. Using the interfaces, clinicians can track their affected patient population by selecting a particular advisory notification and viewing the patients that may be susceptible to that advisory.

Accordingly, the system disclosed herein transforms advisory notification data into an actionable workflow within a time period (e.g., 48 hours) of the advisory being announced while enabling clinics to quickly identify patients under that recall. The clinic can follow patients by opting them in or out of that advisory and can track the status of that patient with that device/lead. Moreover, the clinic personnel can use the clinic system to bucket various workflow stages and easily pick them back up, keep a history of all actions and notes, and immediately identify new patients under an advisory notification when their in-office data is uploaded. Further benefits can be realized by providing a comprehensive view of all the advisory notifications that the clinic is tracking, while also generating clinic behavior analytics to track time and actions spent to resolve the different advisory notifications. Additional advantages will become apparent from the disclosure herein.

FIG. 1 illustrates an example system 100 including a cardiac device advisory management platform 102 to track and manage advisory notification(s) 104 for one or more clinic system(s) 106. The advisory notification(s) 104 can originate from a manufacturer 108 and/or from a Federal Drug Administration (FDA) system, which can be received 6-8 weeks later than advisory notifications 104 received directly from the manufacturer 108. The cardiac device advisory management platform 102 can perform data extraction and aggregation procedure(s) 110 to create a new advisory record including advisory notification data 112 extracted from the advisory notification(s) 104 and stored at one or more advisory notification database(s) 114. Accordingly, a clinic user interface (UI) 116 generated by the cardiac device advisory management platform 102 can be presented at a clinic device 118 operating an advisory notification monitoring system 120 to receive the advisory notification data 112 and integrate the advisory notification data 112 into various workflow procedures 122 for the clinic system 106.

The advisory notification data 112 can be extracted and aggregated by the cardiac device advisory management platform 102 and combined with patient data 124 received and stored by the clinic system(s) 106 during one or more onboarding procedures 126. For instance, the advisory notification data 112 can be stored at the advisory notification database(s) 114 to be retrieved by the clinic system(s) 106 and can include one or more of an advisory title, an advisory date, a short description, a long description, a link to a website or more information related to the manufacturer 108, an advisory classification, a recommended action, a manufacturer name, a device and/or lead model, a device number, a device type, a device serial number, combinations thereof, and the like. In some instances, in response to receiving the advisory notification(s) 104 and extracting and storing the advisory notification data 112 in the database(s) 114, the cardiac device advisory management platform 102 sends a message 128 to the clinic system(s) 106 to cause the clinic UI 116 to present one or more indications of the advisory notification data 112 (e.g., at an advisory notification page of a cardiac device management or workflow platform). The advisory notification data 112 can be further stored at a clinic database 130 and/or integrated into the various workflow procedures 122, as discussed in greater detail below.

Figure 2:
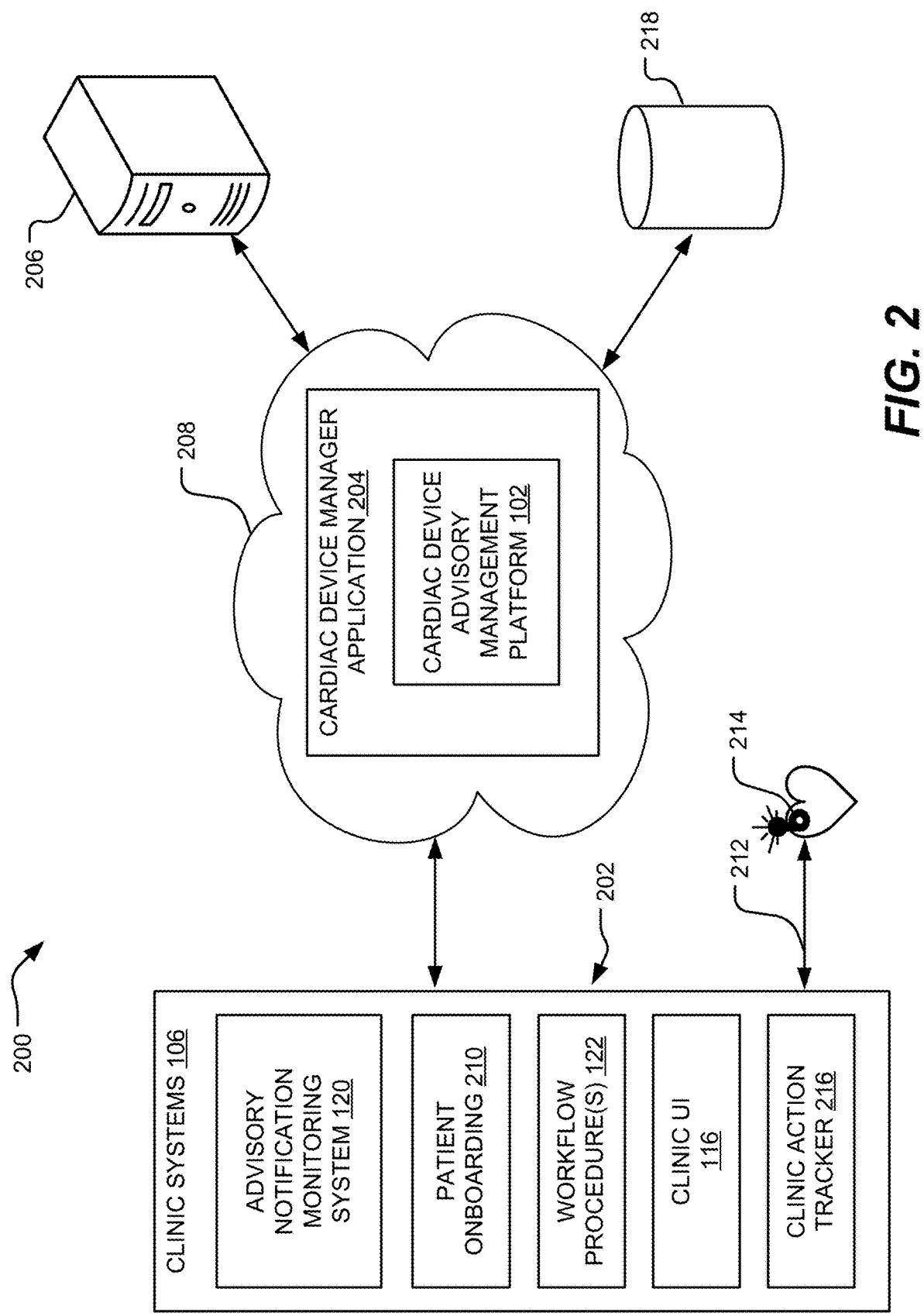
FIG. 2 illustrates an example system to track and distribute advisory notification data for one or more clinic system (s) connected to a network, which can form at least a portion of the system of FIG. 1.

FIG. 2 illustrates an example system 200 to track and manage advisory notification(s) 104 using the cardiac device advisory management platform 102, which can form at least a portion of the system 100 depicted in FIG. 1. As shown in FIG. 2, the system 200 can include one or more clinic system(s) 106 with various clinic services 202. Moreover, the cardiac device advisory management platform 102 can be provided as part of a device manager application 204, as discussed in greater detail below.

In some examples, the clinic system(s) 106 can execute the device manager application 204 including the cardiac device advisory management platform 102 locally at the clinic device 118, remotely as a cloud-based service, (e.g., at a device management platform server 206), or combinations thereof. The device management platform server 206 can be a single server, a plurality of servers with each such server being a physical server or a virtual machine, or a collection of both physical servers and virtual machines. In another implementation, a cloud hosts one or more components of the cardiac device advisory management platform 102. One or more server devices including the device management platform server 206 may represent an instance among large instances of application servers in a cloud computing environment, a data center, or other computing environment.

The cardiac device advisory management platform 102 can provide the advisory notification monitoring system 120 to the clinic system(s) 106 as a downloadable application and/or as a web portal, for instance, accessible via one or more network(s) 208. The network(s) 208 can include one or more of a wide area network (WAN) (e.g., the Internet), over a local area network (LAN), over a cellular network (e.g., third generation (3G), fourth generation (4G), Long-Term Evolution (LTE), fifth generation (5G), Ethernet, Wi-Fi, Bluetooth®, Near Field Communication (NFC), and the like. The clinic system(s) 106 can access any of the various clinic services 202 provided by the cardiac device advisory management platform 102 via the network(s) 208 and/or data stored locally at the clinic database 130.

In some examples, the cardiac device advisory management platform 102 provides a variety of clinic services 202 to the system(s) 106 related to managing and tracking the advisory notifications 104 and corresponding workflow procedures 122. The clinic services 202 can collectively be considered the advisory notification monitoring system 120 and/or sub-components of the advisory notification monitoring system 120. For instance, the clinic services 202 can include the onboarding procedures 126, such as a patient onboarding procedure 210. The patient onboarding procedure 210 can be performed before, during, or after implementing the cardiac device advisory management platform 102 to generate and/or receive the patient data 124 at the clinic system 106. The patient onboarding procedure 210 can include checking to see if a device or lead of a new patient is under one of the advisory notifications 104 the cardiac device advisory management platform 102 is already tracking; uploading serial numbers and verifying the serial numbers (e.g., by comparing the serial numbers to a list of previously identified common variations of the serial number); tagging matched serial numbers from a patient list (e.g., stored at the clinic database 130); populating the patient list with specific devices and/or leads in the new patient data; opting the patient into being followed for one or more advisory notification(s) 104 (e.g., in response to a clinician input at the UI 116); displaying (e.g., at the clinic UI 116) an advisory notification 104 with an option that can be selected to opt a patient (e.g., a new patient or a patient already in the patient list) into tracking for the advisory notification 104 (e.g., with details of the advisory notification overlayed). Moreover, the onboarding procedures 126 can include an in-office patient onboarding procedure for inputting data received from a patient performing an in-office visit at the clinic. For instance, interrogation data 212 can be extracted and received from an implanted cardiac device 214 during an in-office visit of the patient, and the cardiac device advisory management platform 102 can check to see if the implanted cardiac device 214 (e.g., and/or a lead of the implanted cardiac device 214) is under one of the advisory notification(s) 104 received by the cardiac device advisory management platform 102. Moreover, the patient from which the interrogation data 212 was received can be opted into tracking for one or more advisory notifications 104 for similar or identical cardiac devices.

In some examples, the clinic services 202 can include the workflow procedures 122. For instance, the device manager application 204 can include multiple different windows, tabs, drop down menus, panels, and the like (e.g., as depicted in FIGS. 4-9) and a series of workflow operations to provide the workflow procedures 122 via the clinic UI 116. The advisory notification data 112 can be integrated into the different workflow procedures 122 in multiple ways, for instance, by generating one or more action indicators, as discussed below regarding FIG. 3. Furthermore, a clinic action tracker 216 can track and analyze clinic action data generated by the various workflow procedures 122. Various clinic inputs discussed herein can be recorded as clinic action data with timestamps such that a series of operations performed for the various workflow procedures 122 can be quantified and stored for further analysis. The clinic action tracker 216 can analyze the clinic action data and output results indicating, for instance, an average amount of time to change a patient status (as discussed in greater detail below regarding FIG. 3); an average amount of workflow time corresponding to a particular advisory notification 104; an average amount of workflow time corresponding to a particular manufacturer 108; and various other determinations based on clinic action data. The outputted results can be specified for a particular clinic, a particular site of the clinic, a particular class of employees (e.g., physicians, nurses, administrative staff, etc.), particular employees, and the like.

In some instances, the device manager application 204 and the cardiac device advisory management platform 102 can access one or more databases 218 including the advisory notification database(s) 114, the clinic database 130, and/or other databases such as a manufacturer database, an FDA database, combinations thereof and the like. In some instances, the one or more databases 218 can store the associations between these different data files. Moreover, the data in the database(s) 218 can be aggregated and associated with patient profiles associated with the cardiac device advisory management platform 102 and/or the clinic system 106 to perform the operations discussed herein.

Figure 3:
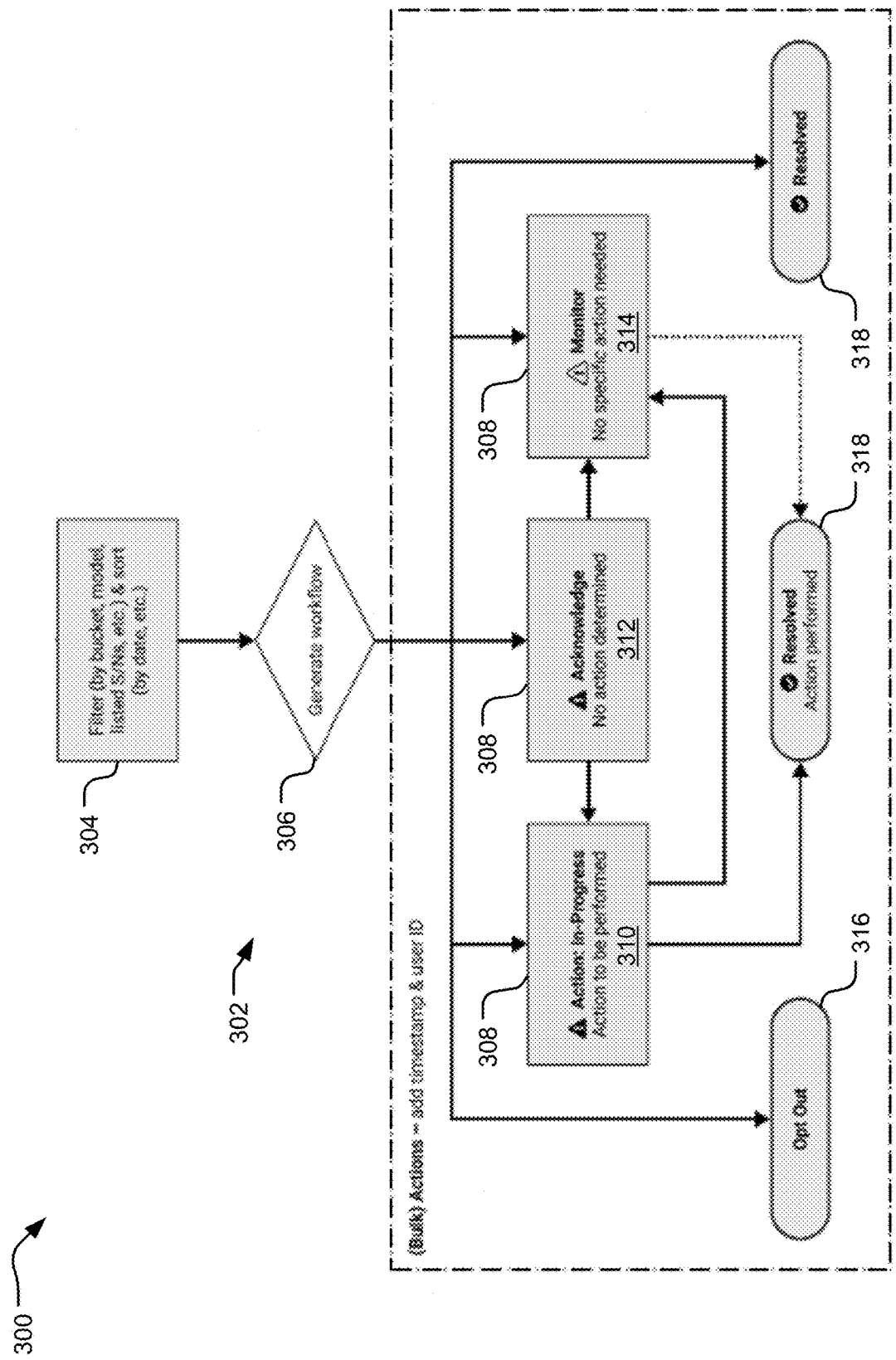
FIG. 3 illustrates an example system to track and distribute advisory notification data by integrating the advisory notification data into various workflow procedures at a clinic system, which can form at least a portion of the system of FIG. 1.

FIG. 3 illustrates an example system 300 to track and manage advisory notification(s) 104 using the cardiac device advisory management platform 102, which can form at least a portion of the system 100 depicted in FIG. 1. As shown in FIG. 3, the system 300 can integrate the advisory notification data 112 into the workflow procedures 122 by performing workflow integration steps 302 with the advisory notification(s) 104.

In some examples, the workflow integration steps 302 can include a filtering operation 304. The filtering operation 304 can filter a list stored in the one or more databases 218 by bucket, device model, listed serial numbers, or any of the data types discussed herein. The filtering operation 304 can include or be followed by a sorting operation (e.g., by date, patient illness type, patient characteristic, etc.). The workflow integrations steps 302 can be initiated by one or more (e.g., a series of) clinician inputs at the clinic UI 116. Upon filtering and sorting, the cardiac device advisory management platform 102 can perform a workflow generation operation 306 in which one or more action indicators 308 are generated and/or presented (e.g., as part of workflow procedures 122.) The action indicators 308 can include an in-progress indicator 310 to indicate that an action is to be performed; an acknowledge indicator 312 to indicate that no action is determined; and/or a monitor indictor 314. Furthermore, the one or more action indicators 308 can be changed to an opted out status 316 and/or an action resolved status 318 (e.g., in response to a clinic action being performed). In some instances, the opted-out status 316 can be a top level or primary status that is usually selected. Furthermore, in some instances, the opted-in status has a work flow with an end state corresponding to a resolve status or monitor status. The cardiac device advisory management platform 102 can generate and aggregate timestamps and user IDs associated with the workflow integration steps 302 and the workflow procedures 122 as they are performed at the clinic UI 116. In some instances, one or more indications of the advisory notification(s) 104 can be sent to and/or presented at a patient device (e.g., a patient computer or patient mobile device), from the clinic device 118 or another device of the cardiac device advisory management platform 102, at least partly in response to a clinician input selecting to send the information to the patient device.

Figure 4:
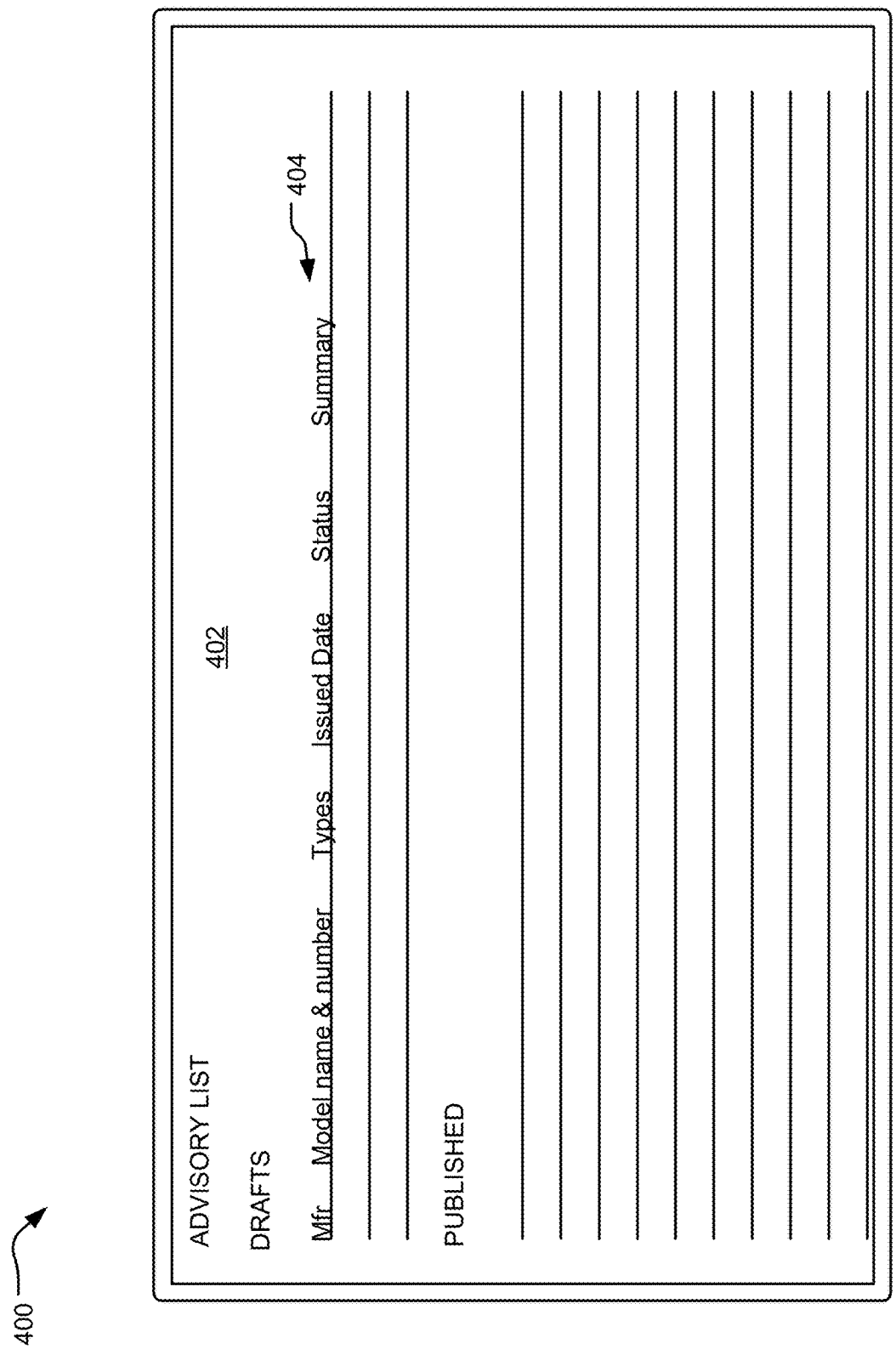
FIG. 4 illustrates an example system to track and distribute advisory notification data using an advisory status interface, which can form at least a portion of the system of FIG. 1.

FIG. 4 illustrates an example system 400 to track and manage advisory notification(s) 104 using the cardiac device advisory management platform 102, which can form at least a portion of the system 100 depicted in FIG. 1. As shown in FIG. 4, the system 400 can include an advisory status interface 402.

For instance, the advisory status interface 402 can be one or more lists generated by the cardiac device advisory management platform 102. The advisory status interface 402 can include a first list of advisory notifications 104 that are drafts of advisory notifications 104 which are not yet published (e.g., distributed for dissemination in a downstream data flow). The advisory status interface 402 can include a second list of advisory notifications 104 that are published advisory notifications 104 and have data which has been stored and is accessible to the workflow procedures 122 of the clinic systems 106.

In some instances, the various lists generated by the advisory status interface 402 can include advisory notification data parameters 404 (e.g., as data columns). The advisory notification data parameters can include a manufacturer data (e.g., with an abbreviated manufacturer ID); model name and number data, advisory notification type (e.g., lead, ICD, CRT-D, IPG, and the like), issued date of the advisory notification 104; status of the advisory notification(s) 104 (e.g., ongoing, terminated, etc.); summary of the advisory notification(s) 104; combinations thereof; and the like. A first example data entry in the advisory status interface 402 with the advisory notification data parameters 404 is "Mfr: BSX; Model Name and number: EMBLEM MRI S-ICD A219 S-ICD; Type: ICD; Issued: Feb. 28, 2020; Status: ongoing; Summary: Boston Scientific EMBLEM S-ICD Advisory with Elevated Likelihood for Early replacement." A second example data entry in the advisory status interface 402 with the advisory notification data parameters 404 is "Mfr: STJ; Model name and number: Riata 1470, Riata 151, Riata 1572, Riata 1580; Types: Lead; Issued Feb. 28, 2020; Status: ongoing; Summary: HV lead abrasion leading to externalized conductors." The advisory status interface 402 can be presented at a computing device associated with the cardiac device advisory management platform 102 (e.g., a third-party provider of the cardiac device advisory management platform 102 and the device manager application 204), and/or the clinic UI 116.

Figure 5A:
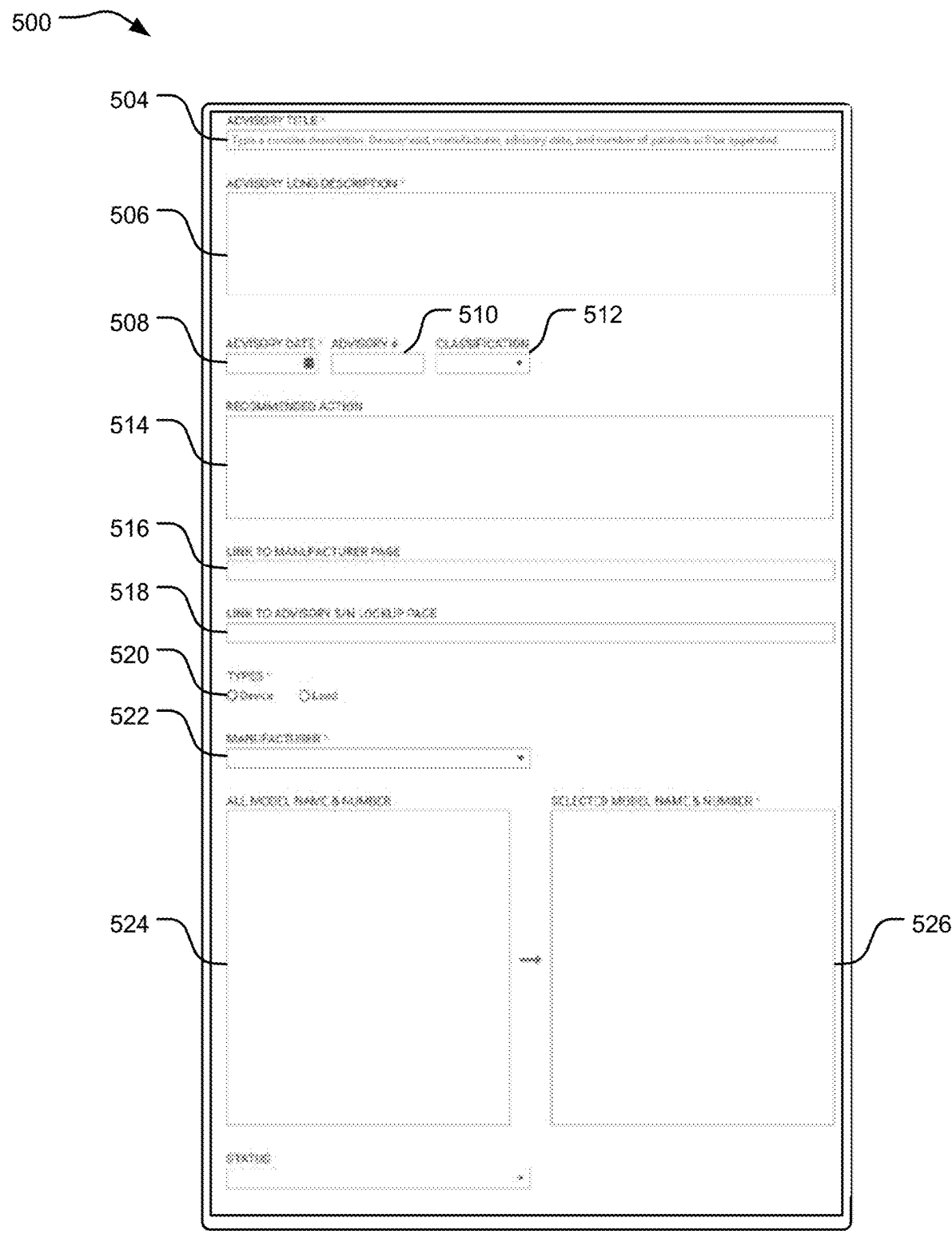
FIGS. 5A and 5B illustrate an example system to track and distribute advisory notification data using a data extraction interface, which can form at least a portion of the system of FIG. 1.
Figure 5B:
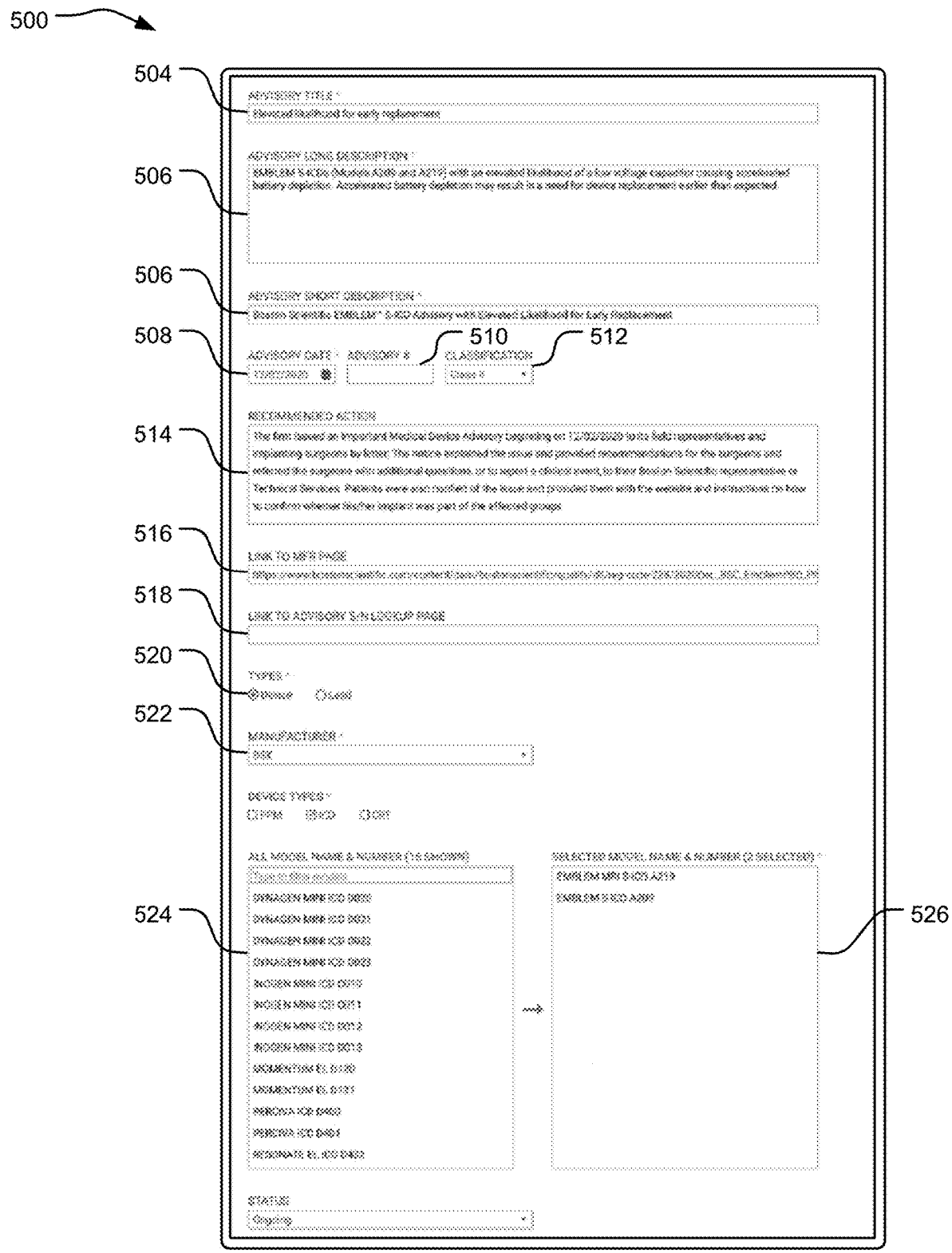

FIGS. 5A and 5B illustrate an example system 500 to track and manage advisory notification(s) 104 using the cardiac device advisory management platform 102, which can form at least a portion of the system 100 depicted in FIG. 1. As shown in FIGS. 5A and 5B, the system 500 can include a data extraction interface 502, which can be used as part of the data extraction and aggregation procedure(s) 110.

In some examples, the data extraction interface 502 can be presented at a user interface (e.g., associated with the cardiac device advisory management platform 102 and/or as part of the clinic UI 116) as one or more fields 504 to be populated with the different data types from the advisory notification data 112. Additionally or alternatively, the data corresponding to the fields 504 can be aggregated on the back-end without presenting a UI. In other words, the fields 504 can be populated manually and/or a text recognition algorithm or other trained algorithm can automatically extract the advisory notification data 112 from the advisory notification(s) 104 and populate some or all of the fields 504. The data types corresponding to the fields 504 can include an advisory notification title; an advisory description 506 (e.g., a short description and/or a long description); an advisory date 508; an advisory number 510; an advisory classification 512; and/or a recommended action 514. Furthermore, the data extraction interface 502 can include a link to a manufacturer page or information 516; a link to an advisory serial number lookup page 518; a type of advisory notification 520 (e.g., device or lead); a manufacturer 522; a list of all or related model names and numbers 524; and/or a list of selected model names and number 526. The data extraction interface 502 can determine model name or model variations that are associated with a particular advisory notification(s) 104.

The data extraction interface 502 can extract the advisory notification data 112, separate it into the different data types, and store the extracted and aggregated data in the advisory notification database(s) 114. By using this technique, different formats of various advisory notification(s) 104 from different manufacturers 108 can be generated using a consistent and streamlined procedure independent of the different formats used by the manufacturers 108 By using machine learning feedback loops with error correction and training data sets, various text recognition and extraction procedures can be performed on the advisory notification(s) 104 to recognize the different data file names and texts to create data entries corresponding to the fields 504. Accordingly, the advisory notification data 112 can be generated from the advisory notification(s) 104 via data extraction and aggregation procedure(s) 110 using manual techniques, automated or machine learning-assisted techniques, or both.

Figure 6:
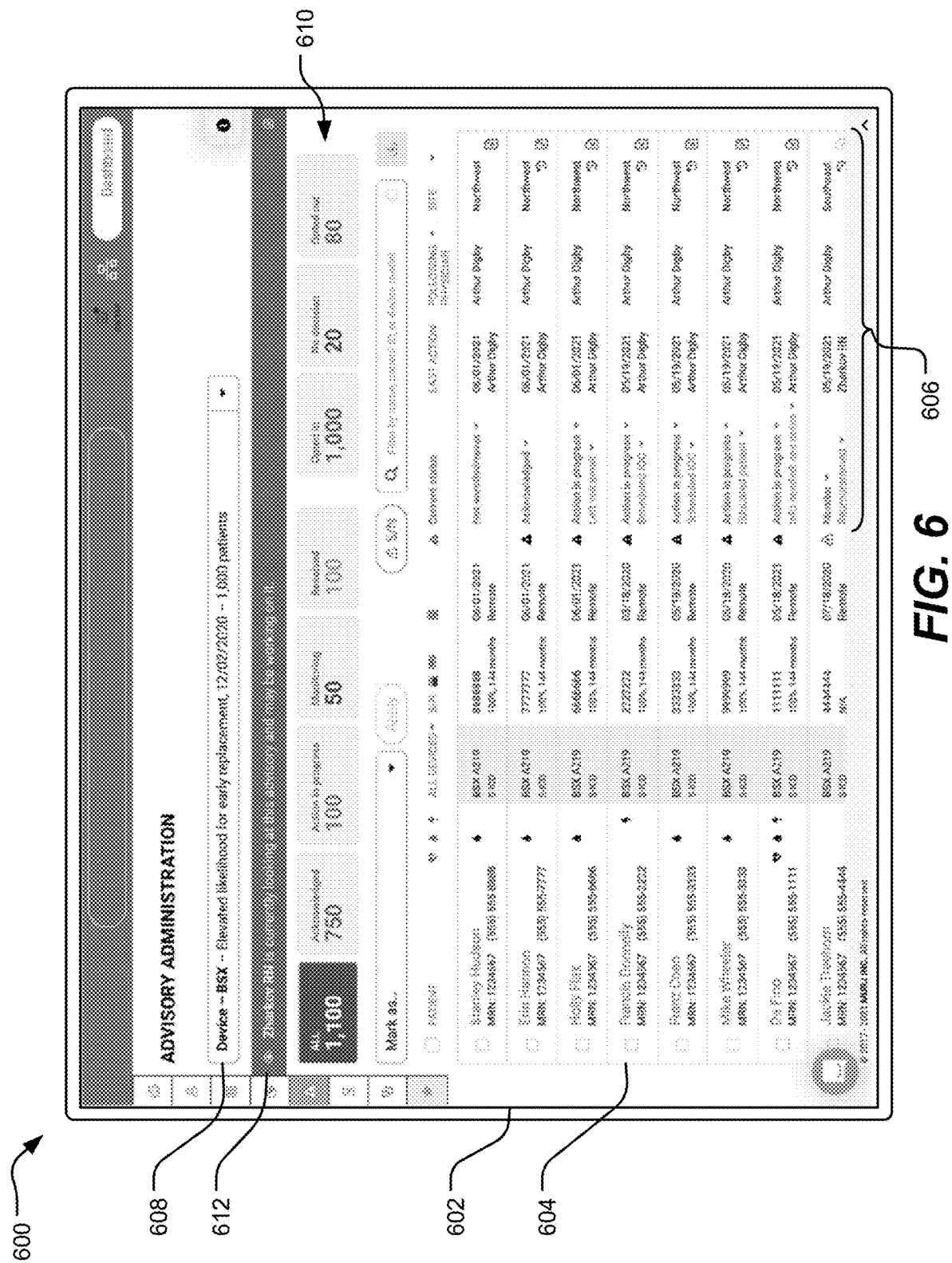
FIG. 6 illustrates an example system to track and distribute advisory notification data using an advisory administration interface, which can form at least a portion of the system of FIG. 1.

FIG. 6 illustrates an example system 600 to track and manage advisory notification(s) 104 using the cardiac device advisory management platform 102, which can form at least a portion of the system 100 depicted in FIG. 1. As shown in FIG. 6, the system 600 can include an advisory administration interface 602 for viewing the advisory notification data 112.

The cardiac device advisory management platform 102 can present the advisory administration interface 602 as a selectable tab of the device manager application 204. Upon navigating to the advisory administration interface 602, the advisory notification data 112 can be presented as a list (e.g., a filtered list) of patients 604, which can list a patient name, a device name or number, a dated device monitoring type (e.g., remote, in-office, etc.), a current status (e.g., including the one or more action indicators 308), a last action taken (e.g., left voice mail, scheduled in-office consultation, educated patient, reprogrammed device, more info needed see notes, and the like). The list of patients 604 can further present clinic action data 606 including an action or last action taken data (e.g., a date, a name of personnel, an action description), a following up physician, and/or a clinic site name.

In some examples, the advisory administration interface 602 includes an advisory notification input portion 608 for creating or filtering the indications for only those related to a particular advisory notification data 112. The advisory administration interface 602 can further include other portions including other indications of the advisory notification data 112. For instance, the advisory administration interface 602 can include advisory notification analytics values 610 calculated by determining metrics of the patient data 124 related to the particular advisory notification data 112. The advisory notification analytics values 610 can include calculations of values such as a total amount of patients or devices affected by the particular advisory notification(s) 104; a number of patients or devices having an acknowledged status; a number of patients or devices having an in-progress status; a number of patients or devices having a monitoring status; a number of patients or devices having a resolved status; a number of patients or devices opted in to tracking; a number of patients or devices opted out of tracking; a number of patients or devices with no opt in decision; and/or combinations thereof. Moreover, the advisory administration interface 602 can generate a currently viewing indicator 612 indicating a name of clinic personnel currently viewing the advisory notification 104.

In some instances, the advisory notification analytics values 610 and/or other advisory notification data indications can be selectable elements and/or associated with subsets of the patient list such that receiving inputs at these data indications generates the filtered list related to that particular metric. For instance, selecting the advisory notification analytics values 610 indicating the total number of patients or device with the "in-progress" status for a particular advisory notification 104 can cause the cardiac device advisory management platform 102 to filter the list of patients 604 to show only patients or devices with the "in-progress" status. The advisory notification analytics values can be associated with the advisory notification data parameters 404 and other advisory notification data 112 (e.g., which can be presented as an advisory detail panel overlayed onto the list of patients 604). The cardiac device advisory management platform 102 can receive an upload of a serial number (e.g., via a CSV. file upload) of serial numbers of devices or leads to be added to the particular advisory notification(s) 104 presented at the advisory administration interface 602. The listed patients affected by the advisory notification(s) 104 can be bulk selected to have marked as a particular status in bulk (e.g., as "monitor").

Figure 7:
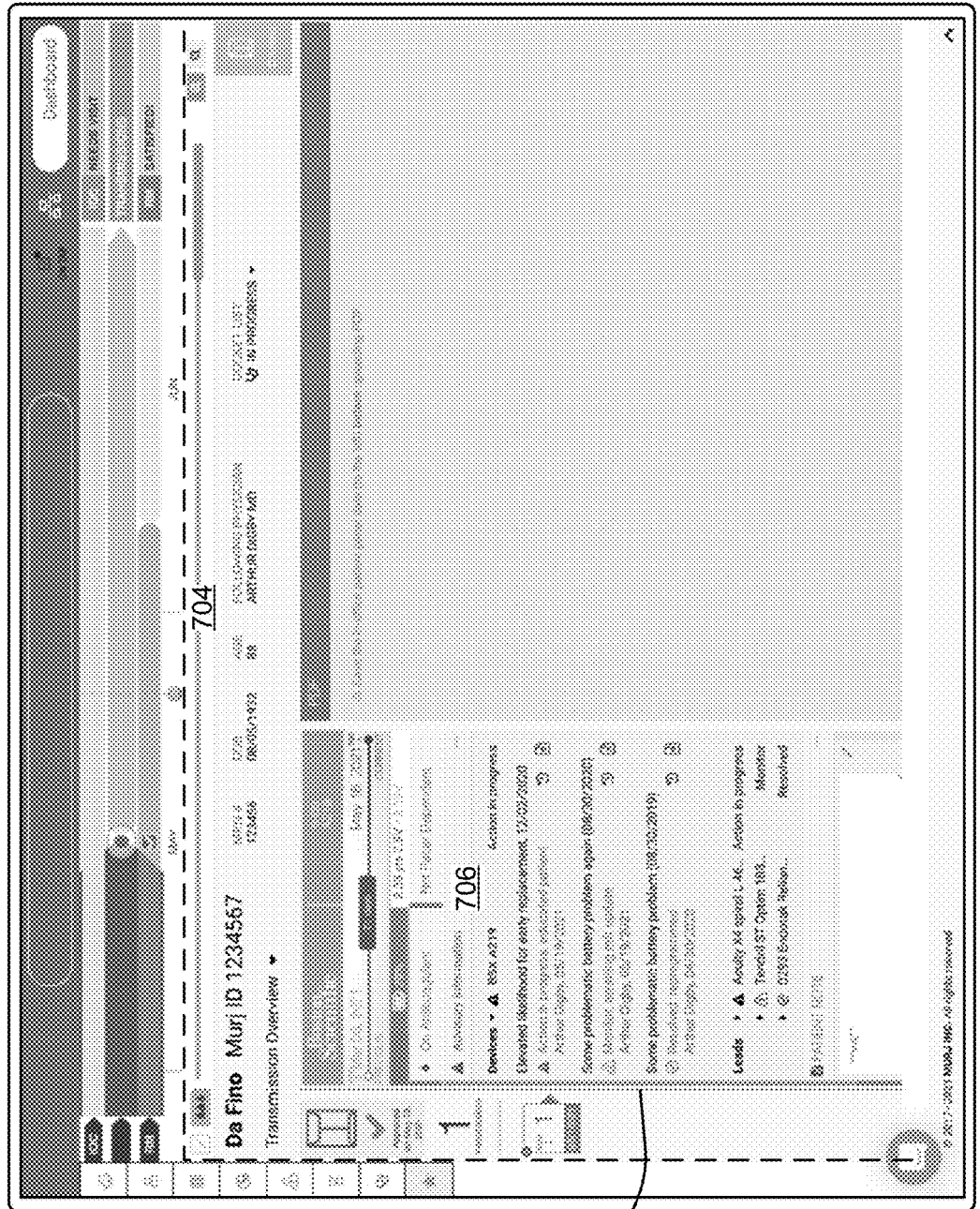
FIG. 7 illustrates an example system to track and distribute advisory notification data using a patient panel, which can form at least a portion of the system of FIG. 1.

FIG. 7 illustrates an example system 700 to track and manage advisory notification(s) 104 using the cardiac device advisory management platform 102, which can form at least a portion of the system 100 depicted in FIG. 1. As shown in FIG. 7, the system 700 can include a patient panel 702 for presenting the indications of the advisory notification data 112.

For instance, the patient panel 702 can form a part of or be layered over a patient page 704 of the device manager application 204. The patient panel 702 can present advisory notification related information specific to a particular patient, such as a monitoring period duration and number of days into the monitoring period, a device battery level, age, and/or voltage, and/or other additional advisory notification information. Additional information 706 (e.g., in the patient panel 702) related to the patient and/or the advisory notification(s) 104 can be presented in response to additional clinic inputs at the clinic UI 116, for instance, selecting the patient from the patient list 604 and/or clinic inputs at other clinic UI 116 components (e.g., from the patient page 704 of the device manager application 204). The additional information 706 can include a device identifier, an action identifier, a list of advisory notification summaries, a list of advisory notification dates, a list of clinic personnel and clinic personnel actions, a list of lead types, a list of lead statuses, patient notes, combinations thereof, and the like. The patient panel 702 can be generated and/or presented simultaneously with a patient identifier, a platform identifier, a date of birth, an age, a following physician, a docket list status (e.g., in progress, resolved, acknowledged, etc.), and combinations thereof.

Figure 8:
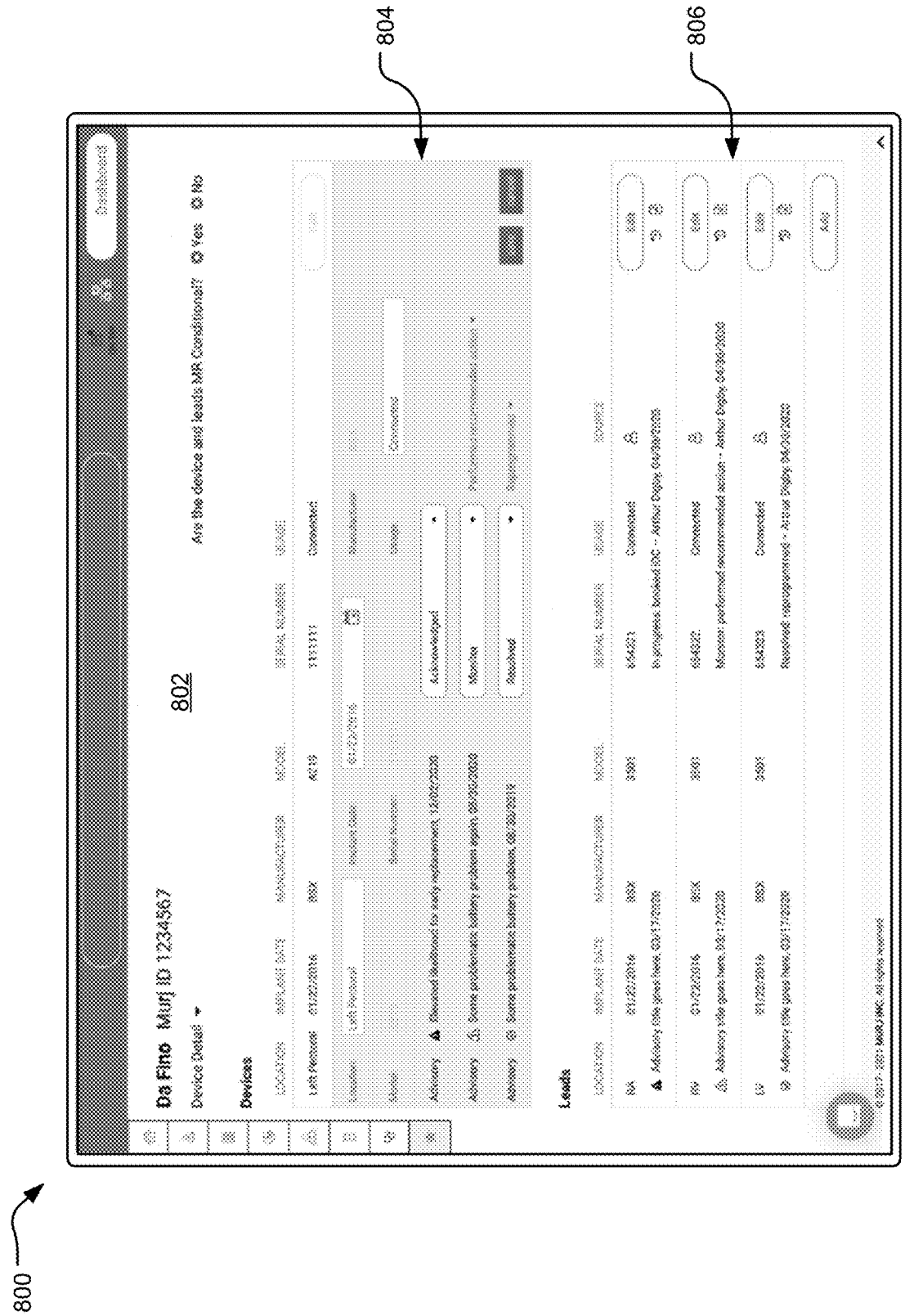
FIG. 8 illustrates an example system to track and distribute advisory notification data using a device detail interface, which can form at least a portion of the system of FIG. 1.

FIG. 8 illustrates an example system 800 to track and manage advisory notification(s) 104 using the cardiac device advisory management platform 102, which can form at least a portion of the system 100 depicted in FIG. 1. As shown in FIG. 8, the system 800 can include a device detail interface 802 for presenting the indications of the advisory notification data 112.

For instance, the device detail interface 802 can include a device information section 804 and/or a lead information section 806. The device information section 804 can include a list of one or more implanted cardiac device(s) (e.g., different selectable devices) and details about the implanted cardiac device such as a location in the body, an implant date, a manufacturer, a model number, a serial number, a usage status, as well as a list of advisory notifications, short summaries, action indicator statuses, and advisory dates, a patient illness, a patient characterization, and the like.

The lead information section 806 can include information related to particular leads of an implanted cardiac device, such as the implanted cardiac device selected in the device information section 804. This lead-related information can be a lead location (e.g., a heart implant location), an implant date, a manufacturer, a model number, a serial number, a usage status, an action indicator, a clinic personnel that performed the action, and an action date. In some examples, one or more clinician inputs (e.g., at the device detail interface 802) can cause device and lead information related to multiple different manufacturers to be aggregated and presented together (e.g., simultaneously at the clinic UI 116). The cardiac device advisory management platform 102 can receive multiple different advisory notifications (e.g., a first advisory notification, a second advisory notification, a third advisory notification, etc.). To aggregate this data, the device information (e.g., the cardiac device model identifier, the lead identifier, etc.) can be extracted and stored separately and/or with an association to the advisory notification 104. In this way, the data can be retrieved and combined from different advisory notifications-independent of their initial formats—and formatted together into a single workflow or interface.

Figure 9:
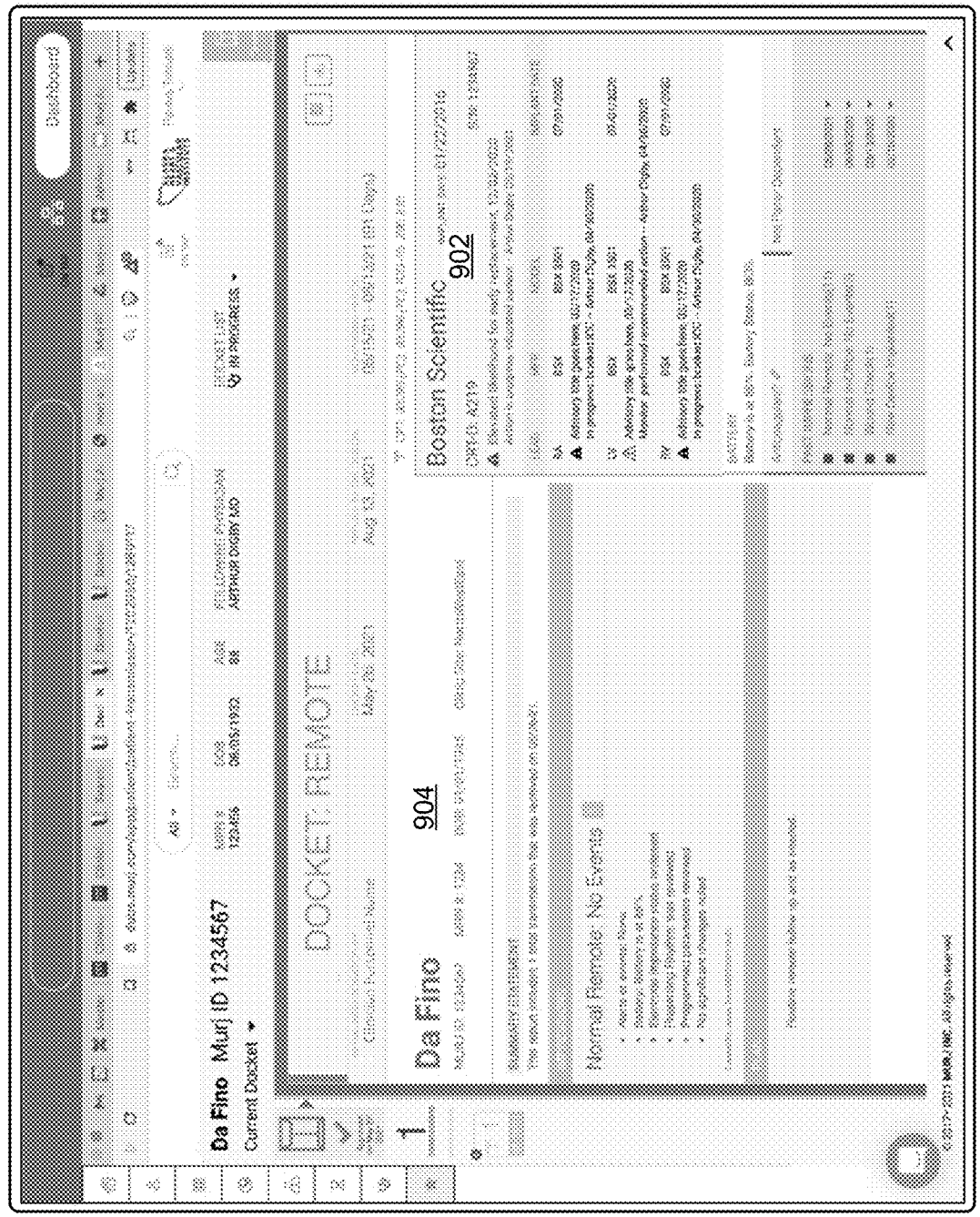
FIG. 9 illustrates an example system to track and distribute advisory notification data using a patient docket advisory notice interface, which can form at least a portion of the system of FIG. 1.

FIG. 9 illustrates an example system 900 to track and manage advisory notification(s) 104 using the cardiac device advisory management platform 102, which can form at least a portion of the system 100 depicted in FIG. 1. As shown in FIG. 9, the system 900 can include a patient docket advisory notice interface 902 for presenting the device data and/or lead data for multiple advisory notifications 104.

In some examples, the patient docket advisory notice interface 902 can form a part of or be generated to be presented simultaneously with a patient docket page 904, which can be navigated to (e.g., via a top or side bar menu) as a part of a various workflow procedures 122 provided by the device manager application 204. For instance, the patient docket page 904 can include additional patient information for a patient associated with the advisory notification(s) 104, including a list or number of cardiac device transmissions received for the patient, a number of alerts or events, a battery percent, an electrode impedance review status, a presenting rhythm review status, whether programming parameters are reviewed, and/or whether any significant changes are noted. In some instances, actions performed by the cardiac device advisory management platform 102 can associate the clinic activity responsive to the advisory notification(s) 104 with one or more CPT codes (e.g., to satisfy one or more billing requirements).

Figure 10:
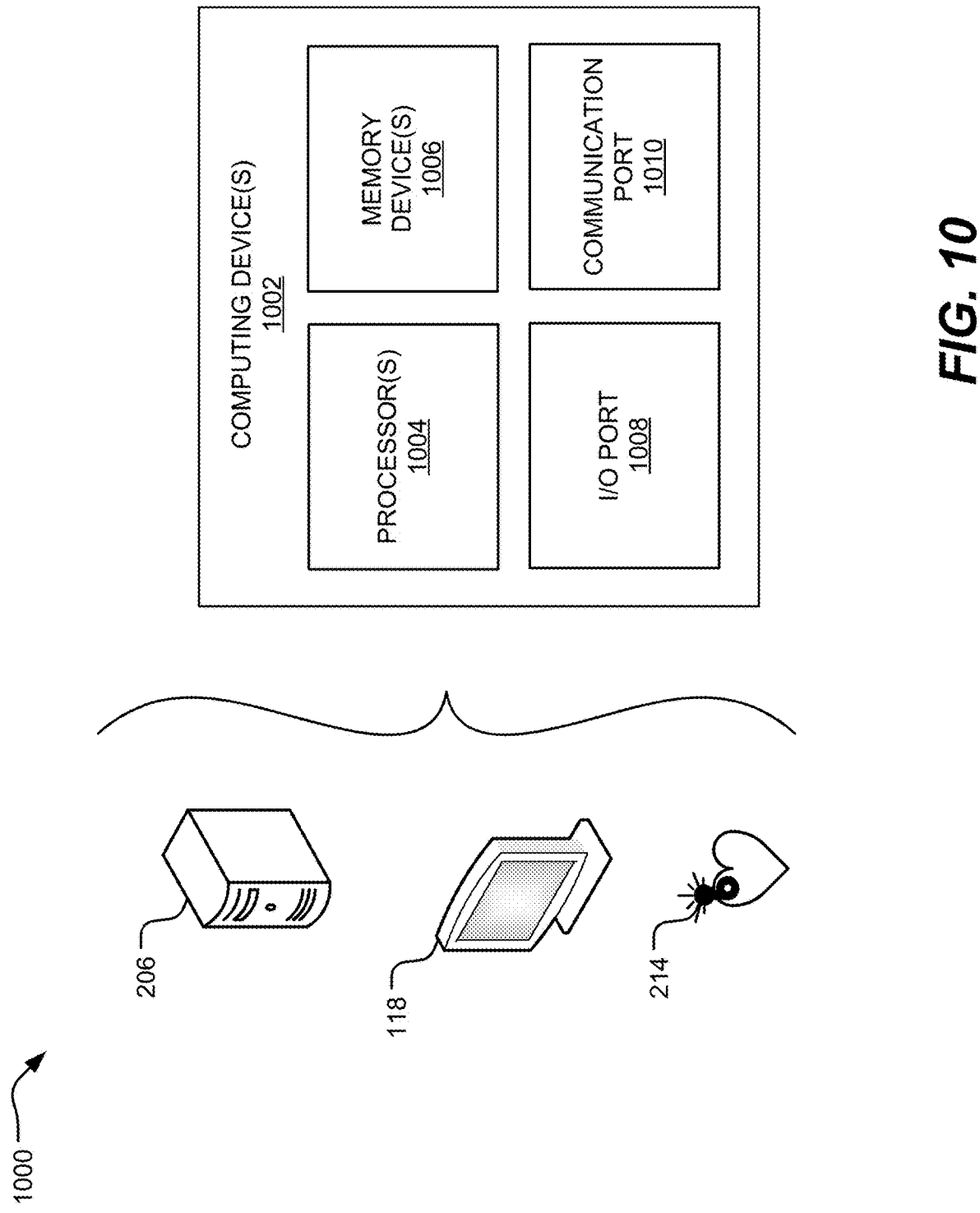
FIG. 10 illustrates an example system to track and distribute advisory notification data using one or more computing devices, which can form at least a portion of the system of FIG. 1.

FIG. 10 illustrates an example system 1000 to provide the cardiac device advisory management platform 102. The system 1000 can include one or more computing device(s) 1002 which can implement the systems 100-900 discussed herein. In one implementation, the one or more computing device(s) 1002 include the clinic device 118, the device management platform server 206, a device management platform computer, the implanted cardiac device 214, a patient personal device (e.g., a patient mobile device), and/or any other devices forming or implementing the systems 100-900.

In some instances, the computing device(s) 1002 includes a computer, a personal computer, a desktop computer, a laptop computer, a terminal, a workstation, a cellular or mobile phone, a mobile device, a smart mobile device a tablet, a wearable device (e.g., a smart watch, smart glasses, a smart epidermal device, etc.) a multimedia console, a television, an Internet-of-Things (IoT) device, a smart home device, a medical device, a virtual reality (VR) or augmented reality (AR) device, a vehicle (e.g., a smart bicycle, an automobile computer, etc.), combinations thereof, and/or the like. The computing device(s) 1002 may be integrated with, form a part of, or otherwise be associated with the systems 100-900. It will be appreciated that specific implementations of these devices may be of differing possible specific computing architectures not all of which are specifically discussed herein but will be understood by those of ordinary skill in the art.

The computing device 1002 may be a computing system capable of executing a computer program product to execute a computer process. The cardiac device advisory management platform 102 and/or the device manager application 204 can be stored and executed at the computing device 1002 (e.g., as one or more software components). Data and program files may be input to the computing device 1002 (e.g., the advisory notification(s) 104, the patient data 124, the clinician inputs, etc.) which reads the files and inputs and executes the programs therein to generate the cardiac device advisory management platform 102. Some of the elements of the computing device 1002 include one or more hardware processors 1004, one or more memory devices 1006, and/or one or more ports, such as input/output (IO) port(s) 1008 and communication port(s) 1010. Additionally, other elements that will be recognized by those skilled in the art may be included in the computing device 1002 but are not explicitly depicted in FIG. 10 or discussed further herein. Various elements of the computing device 1002 may communicate with one another by way of the communication port(s) 1010 and/or one or more communication buses, point-to-point communication paths, or other communication means.

The processor 1004 may include, for example, a central processing unit (CPU), a microprocessor, a microcontroller, a digital signal processor (DSP), and/or one or more internal levels of cache. There may be one or more processors 1004, such that the processor 1004 comprises a single central-processing unit, or a plurality of processing units capable of executing instructions and performing operations in parallel with each other, commonly referred to as a parallel processing environment.

The computing device 1002 may be a conventional computer, a distributed computer, or any other type of computer, such as one or more external computers made available via a cloud computing architecture. The presently described technology is optionally implemented in software stored on the data storage device(s) such as the memory device(s) 1006, and/or communicated via one or more of the ports 1008 and 1010, thereby transforming the computing device 1002 in FIG. 10 to a special purpose machine for implementing the operations described herein.

The one or more memory device(s) 1006 may include any non-volatile data storage device capable of storing data generated or employed within the computing device 1002, such as computer executable instructions for performing a computer process, which may include instructions of both application programs and an operating system (OS) that manages the various components of the computing device 1002. The memory device(s) 1006 may include, without limitation, magnetic disk drives, optical disk drives, solid state drives (SSDs), flash drives, and the like. The memory device(s) 1006 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory device(s) 1006 may include volatile memory (e.g., dynamic random-access memory (DRAM), static random-access memory (SRAM), etc.) and/or non-volatile memory (e.g., read-only memory (ROM), flash memory, etc.).

Computer program products containing mechanisms to effectuate the systems and methods in accordance with the presently described technology may reside in the memory device(s) 1006 which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computing device 1002 includes one or more ports, such as the I/O port 1008 and the communication port 1010, for communicating with other computing devices and/or the network 208. It will be appreciated that the I/O port 1008 and the communication port 1010 may be combined or separate and that more or fewer ports may be included in the computing device 1002.

The I/O port 1008 may be connected to an I/O device, or another device, by which information is input to or output from the computing device 1002. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing device 1002 via the I/O port 1008. Similarly, the output devices may convert electrical signals received from the computing device 1002 via the I/O port 1008 into signals that may be sensed as output by a human, such as sound, light, and/or touch. The input device may be an alphanumeric input device, including alphanumeric and other keys for communicating information and/or command selections to the processor 1004 via the I/O port 1008. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

In one implementation, the communication port 1010 is connected to the network 208 and the computing device 1002 may receive network data useful in executing the methods and systems set out herein as well as transmitting information and network configuration changes determined thereby. Stated differently, the communication port 1010 connects the computing device 1002 to one or more communication interface devices configured to transmit and/or receive information between the computing device 1002 and other devices by way of one or more wired or wireless communication networks or connections. Examples of such networks or connections include, without limitation, Universal Serial Bus (USB), Ethernet, Wi-Fi, Bluetooth®, Near Field Communication (NFC), and so on. One or more such communication interface devices may be utilized via the communication port 1010 to communicate one or more other machines, either directly over a point-to-point communication path, over a wide area network (WAN) (e.g., the Internet), over a local area network (LAN), over a cellular network (e.g., third generation (3G), fourth generation (4G), Long-Term Evolution (LTE), fifth generation (5G), etc.) or over another communication means. Further, the communication port 1010 may communicate with an antenna or other link for electromagnetic signal transmission and/or reception.

In an example implementation, the cardiac device advisory management platform 102 may be embodied by instructions stored on the memory devices 1006 and executed by the processor 1004.

The system 1000 set forth in FIG. 10 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized. In the present disclosure, the methods disclosed may be implemented as sets of instructions or software readable by the computing device 1002.

Figure 11:
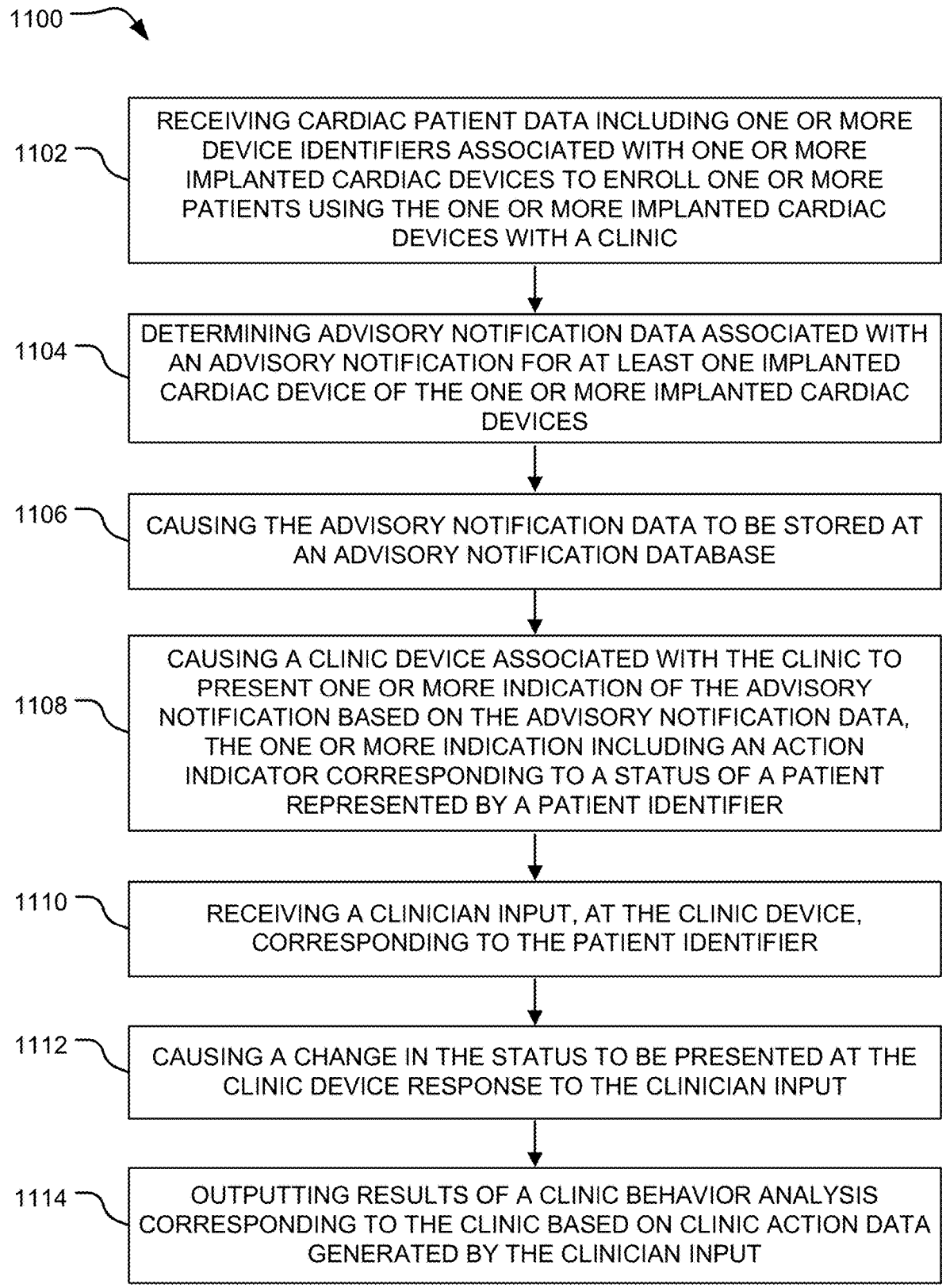
FIG. 11 illustrates an example method to track and distribute advisory notification data using a cardiac device advisory management platform, which can be performed by at least the system of FIG. 1.

FIG. 11 illustrates an example method 1100 to track and manage advisory notification(s) 104 using the cardiac device advisory management platform 102, which can be performed by any of the systems 100-1000.

In some examples, at operation 1102, the method 1100 receives cardiac patient data including one or more device identifiers associated with one or more implanted cardiac devices to enroll one or more patients using the one or more implanted cardiac devices with a clinic. At operation 1104, the method 1100 determines advisory notification data associated with an advisory notification for at least one implanted cardiac device of the one or more implanted cardiac devices. At operation 1106, the method 1100 causes the advisory notification data to be stored at an advisory notification database. At operation 1108, the method 1100 causes a clinic device associated with the clinic to present one or more indication of the advisory notification based on the advisory notification data, the one or more indication including an action indicator corresponding to a status of a patient represented by a patient identifier. At operation 1110, the method 1100 receives a clinician input, at the clinic device, corresponding to the patient identifier. At operation 1112, the method 1100 causes a change in the status to be presented at the clinic device response to the clinician input. At operation 1114, the method 1100 outputs results of a clinic behavior analysis corresponding to the clinic based on clinic action data generated by the clinician input.

It is to be understood that the specific order or hierarchy of steps in the method 1100 depicted in FIG. 11 are instances of example approaches and can be rearranged while remaining within the disclosed subject matter. For instance, any of the operations depicted in FIG. 11 or throughout this disclosure may be omitted, repeated, performed in parallel, performed in a different order, and/or combined with any other of the operations depicted in FIG. 11 or throughout this disclosure.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined differently in various implementations of the disclosure or described with different terminology. These and other variations, modifications, additions, and improvements may fall within the scope of the disclosure as defined in the claims that follow.

What is claimed is:

1. A method for cardiac patient device management, the method comprising:
receiving an advisory notification for one or more cardiac devices issued by at least one of a manufacturer of the cardiac device or a regulatory agency;
determining advisory notification data associated with the advisory notification for the one or more cardiac devices;
storing the advisory notification data at an advisory notification database;
combining the advisory notification data with patient data, the patient data including one or more device identifiers associated with the one or more cardiac devices; and
sending a message to a clinic system to cause a clinic device associated with the clinic system to present one or more indications of the advisory notification data.

2. The method of claim 1, wherein the one or more indications include an action indicator corresponds to a status of a patient represented by a patient identifier, the method further comprising:
causing a first change in the status to be presented at the clinic device responsive to a clinician input received at the clinic device that corresponds to the patient identifier.

3. The method of claim 2, wherein the action indicator corresponds to one or more of:
an in-progress indicator;
an acknowledged indicator;
a monitoring indicator; and
a resolved indicator.

4. The method of claim 2, wherein:
the clinician input is a first clinician input; and
the method further comprises causing a second change in the status to be presented at the clinic device responsive to a second clinician input received at the clinic device that is responsive to the action indicator, the second change causing the status of the patient to be at least one of:
associated with action-in-progress for the advisory notification;
opted-out of tracking for the advisory notification;
opted-in for tracking for the advisory notification; or
monitored for other advisory notifications.

5. The method of claim 1, wherein the advisory notification includes one or more of:
- a link directed to a website of a manufacturer associated with a manufacturer-specific serial number for at least one of the one or more cardiac devices;
- an advisory title;
- an advisory date;
- a description;
- an advisory classification;
- a recommended action;
- a manufacturer name;
- a device and/or lead model;
- a device number;
- a device type; and
- a device serial number.

6. The method of claim 1, wherein:
- the advisory notification is a first advisory notification with a first format corresponding to a first device manufacturer;
- the one or more indications is a first indication;
- the message is a first message; and
- the method further comprises:
  - receiving a second advisory notification with a second format corresponding to a second device manufacturer that is different from the first device manufacturer;
  - storing the second advisory notification at the advisory notification database; and
  - sending a second message to the clinic system to cause the clinic device to present a second indication of the second advisory notification.

7. The method of claim 1, wherein:
- the advisory notification is a first advisory notification for a particular cardiac device model;
- the one or more indications is a first indication;
- the message is a first message; and
- the method further comprises:
  - receiving a second advisory notification for the particular cardiac device model; and
  - sending a second message to the clinic system to cause the clinic device to present, at a clinic user interface (UI), a second indication of the second advisory notification simultaneously with the first indication of the first advisory notification.

8. The method of claim 1, wherein:
- the advisory notification is a first advisory notification for a first lead of at least one of the one or more cardiac devices;
- the one or more indications is a first indication;
- the message is a first message; and
- the method further comprises:
  - receiving second advisory notification data corresponding to a second lead of the at least one of the one or more cardiac devices; and
  - sending a second message to the clinic system to cause the clinic device to present, at a clinic user interface (UI), a second indication of the second advisory notification data simultaneously with the first indication of the first advisory notification.

9. The method of claim 1, wherein the one or more indications of the advisory notification includes a list of patients associated with a device identifier included in the advisory notification.

10. A method for cardiac patient device management, the method comprising:
- receiving an advisory notification for one or more cardiac devices issued by at least one of a manufacturer of the cardiac device or a regulatory agency;
- determining advisory notification data associated with the advisory notification for the one or more cardiac devices;
- combining the advisory notification data with patient data, the patient data including one or more device identifiers associated with the one or more cardiac devices; and
- sending a message to a clinic system to cause a clinic device associated with the clinic system to present one or more indications of the advisory notification data.

11. The method of claim 10, further comprising:
- extracting at least one of a cardiac device model identifier or a lead identifier from the advisory notification; and
- storing the at least one of the cardiac device model identifier or the lead identifier associated with the advisory notification at an advisory notification database accessible to the clinic device.

12. The method of claim 10, further comprising storing the advisory notification data at an advisory notification database to make the advisory notification data accessible to the clinic device within 48 hours of an advisory date included in the advisory notification.

13. The method of claim 10, wherein receiving the advisory notification includes receiving a manufacturer release of the advisory notification that includes one or more of:
- an advisory title;
- an advisory date;
- an advisory description;
- a manufacturer page link;
- an advisory classification;
- a recommended action;
- a device model or lead model;
- a device number;
- a device type; and
- a device serial number.

14. A method for cardiac patient device management, the method comprising:
- receiving an advisory notification for one or more cardiac devices issued by at least one of a manufacturer of the cardiac device or a regulatory agency;
- performing data extraction and aggregation to create advisory notification data extracted from the advisory notification for the one or more cardiac devices;
- storing the advisory notification data at an advisory notification database;
- combining the advisory notification data with patient data acquired during an onboarding procedure by a clinic system, the patient data including one or more device identifiers associated with the one or more cardiac devices; and
- sending a message to the clinic system to cause a clinic device associated with the clinic system to present one or more indications of the advisory notification data.

15. The method of claim 14, wherein the one or more indications includes a list of patients having a cardiac device corresponding to the advisory notification.

16. The method of claim 14, wherein the advisory notification includes one or more of:
- a link directed to a website of a manufacturer associated with a manufacturer-specific serial number for at least one of the one or more cardiac devices;
- an advisory title;
- an advisory date;
- a description;
- an advisory classification;
- a recommended action;
- a manufacturer name;

a device and/or lead model;
a device number;
a device type; and
a device serial number.

* * * * *